United States Patent
Tsuruoka

(10) Patent No.: US 9,645,473 B2
(45) Date of Patent: May 9, 2017

(54) ENDOSCOPE APPARATUS AND CONTROL METHOD FOR ENDOSCOPE APPARATUS

(71) Applicant: OLYMPUS CORPORATION, Shibuya-ku, Tokyo (JP)

(72) Inventor: Takao Tsuruoka, Machida (JP)

(73) Assignee: OLYMPUS CORPORATION, Tokyo (JP)

(*) Notice: Subject to any disclaimer, the term of this patent is extended or adjusted under 35 U.S.C. 154(b) by 400 days.

(21) Appl. No.: 14/312,143

(22) Filed: Jun. 23, 2014

(65) Prior Publication Data

US 2014/0300716 A1 Oct. 9, 2014

Related U.S. Application Data

(63) Continuation of application No. PCT/JP2012/084173, filed on Dec. 28, 2012.

(30) Foreign Application Priority Data

Jan. 17, 2012 (JP) .................................. 2012-006983

(51) Int. Cl.
*G03B 13/00* (2006.01)
*G03B 13/36* (2006.01)
(Continued)

(52) U.S. Cl.
CPC .......... *G03B 13/36* (2013.01); *A61B 1/00006* (2013.01); *A61B 1/00188* (2013.01);
(Continued)

(58) Field of Classification Search
CPC ............................ G03B 13/36; A61B 1/00188
(Continued)

(56) References Cited

U.S. PATENT DOCUMENTS

2007/0055104 A1* 3/2007 Kumei .................. A61B 1/018
600/176
2011/0021872 A1 1/2011 Kumei
(Continued)

FOREIGN PATENT DOCUMENTS

EP 1757221 A1 2/2007
JP 11103409 A 4/1999
(Continued)

OTHER PUBLICATIONS

Extended European Search Report (EESR) dated Mar. 9, 2015 issued in counterpart European Application No. 12866184.0.
(Continued)

*Primary Examiner* — Jeffery Williams
(74) *Attorney, Agent, or Firm* — Holtz, Holtz & Volek PC

(57) ABSTRACT

The endoscope apparatus includes a focus control section that performs a focus control process that controls a plurality of in-focus object plane position, the plurality of in-focus object plane positions being set discretely, a switch control section that switches the focus control process between an autofocus control process and a manual focus control process, and an operation section that is operated by a user, when the operation section has been operated by the user during a period in which the focus control section performs the autofocus control process, the switch control section switching the focus control process from the autofocus control process to the manual focus control process, and the focus control section moving the in-focus object plane position to an in-focus object plane position among the plurality of in-focus object plane positions that differs from the in-focus object plane position when the operation section has been operated.

13 Claims, 10 Drawing Sheets

(51) Int. Cl.
    *A61B 1/00*     (2006.01)
    *G02B 23/24*     (2006.01)
    *H04N 5/232*     (2006.01)
    *H04N 5/225*     (2006.01)

(52) U.S. Cl.
    CPC ..... *G02B 23/2484* (2013.01); *H04N 5/23212* (2013.01); *A61B 1/00039* (2013.01); *H04N 2005/2255* (2013.01)

(58) Field of Classification Search
    USPC .......................................................... 348/65
    See application file for complete search history.

(56) References Cited

U.S. PATENT DOCUMENTS

| | | |
|---|---|---|
| 2011/0058070 A1 | 3/2011 | Awazu |
| 2011/0234781 A1 | 9/2011 | Hackel et al. |

FOREIGN PATENT DOCUMENTS

| | | | |
|---|---|---|---|
| JP | 2004064713 A | 2/2004 |
| JP | 2006288432 A | 10/2006 |
| JP | 2008064980 A | 3/2008 |
| JP | 2008205642 A | 9/2008 |
| JP | 2009142586 A | 7/2009 |
| JP | 2011059337 A | 3/2011 |
| JP | 2011139760 A | 7/2011 |

OTHER PUBLICATIONS

International Search Report (ISR) dated Jan. 29, 2013 issued in International Application No. PCT/JP2012/084173.

\* cited by examiner

ENDOSCOPE APPARATUS AND CONTROL METHOD FOR ENDOSCOPE APPARATUS

CROSS-REFERENCE TO RELATED APPLICATION

This application is a continuation of International Patent Application No. PCT/JP2012/084173, having an international filing date of Dec. 28, 2012, which designated the United States, the entirety of which is incorporated herein by reference. Japanese Patent Application No. 2012-006983 filed on Jan. 17, 2012 is also incorporated herein by reference in its entirety.

BACKGROUND

The present invention relates to an endoscope apparatus, a method for controlling an endoscope apparatus, and the like.

In recent years, the number of pixels of an image sensor used for an endoscope apparatus has been increased, and it has become difficult to capture a deep-focus (pan-focus) image since the aperture is limited due to the diffraction limit. In order to deal with such a situation, JP-A-2011-139760 discloses an endoscope apparatus that performs an autofocus control process (operation) that utilizes an area division/contrast method, for example. According to the technique disclosed in JP-A-2011-139760, the operability of the endoscope apparatus can be improved since the user need not manually control the focus.

JP-A-2011-59337 discloses an imaging device that performs an autofocus control process that utilizes phase difference detection pixels provided in an image sensor. Since the configuration in which the phase difference detection pixels are provided in the image sensor is compact, it is considered that the configuration can also be applied to the end of an endoscope. According to the technique disclosed in JP-A-2011-59337, the autofocus control process can be performed at high speed, and an improvement in operability can be achieved.

JP-A-2009-142586 discloses an endoscope apparatus that is configured so that a focus control mode is switched between an autofocus mode and a manual focus mode based on the brightness level, the magnification, or the like. According to the technique disclosed in JP-A-2009-142586, it is possible to also deal with a scene that is not suitable for the autofocus mode, and an improvement in operability can be achieved.

SUMMARY

According to one aspect of the invention, there is provided an endoscope apparatus comprising:

a focus control section that performs a focus control process that controls a plurality of in-focus object plane positions by controlling an optical system, the plurality of in-focus object plane positions being set discretely;

a switch control section that switches the focus control process performed by the focus control section between an autofocus control process and a manual focus control process, the in-focus object plane position being automatically controlled when the focus control section performs the autofocus control process, and manually controlled when the focus control section performs the manual focus control process; and an operation section that is operated by a user, when the operation section has been operated by the user during a period in which the focus control section performs the autofocus control process, the switch control section switching the focus control process performed by the focus control section from the autofocus control process to the manual focus control process, and the focus control section moving the in-focus object plane position to an in-focus object plane position among the plurality of in-focus object plane positions that differs from the in-focus object plane position when the operation section has been operated by the user.

According to another aspect of the invention, there is provided a method for controlling an endoscope apparatus that controls a plurality of in-focus object plane positions by controlling an optical system, the plurality of in-focus object plane positions being set discretely, the method comprising:

receiving an operation performed by a user;

switching a focus control process between an autofocus control process and a manual focus control process, and moving the in-focus object plane position based on the received operation performed by the user, the in-focus object plane position being automatically controlled when the autofocus control process is performed, and manually controlled when the manual focus control process is performed; and when the operation performed by the user has been received during a period in which the autofocus control process is performed, switching the focus control process from the autofocus control process to the manual focus control process, and moving the in-focus object plane position to an in-focus object plane position among the plurality of in-focus object plane positions that differs from the in-focus object plane position when the operation performed by the user has been received.

DESCRIPTION OF EXEMPLARY EMBODIMENTS

Figure 1:
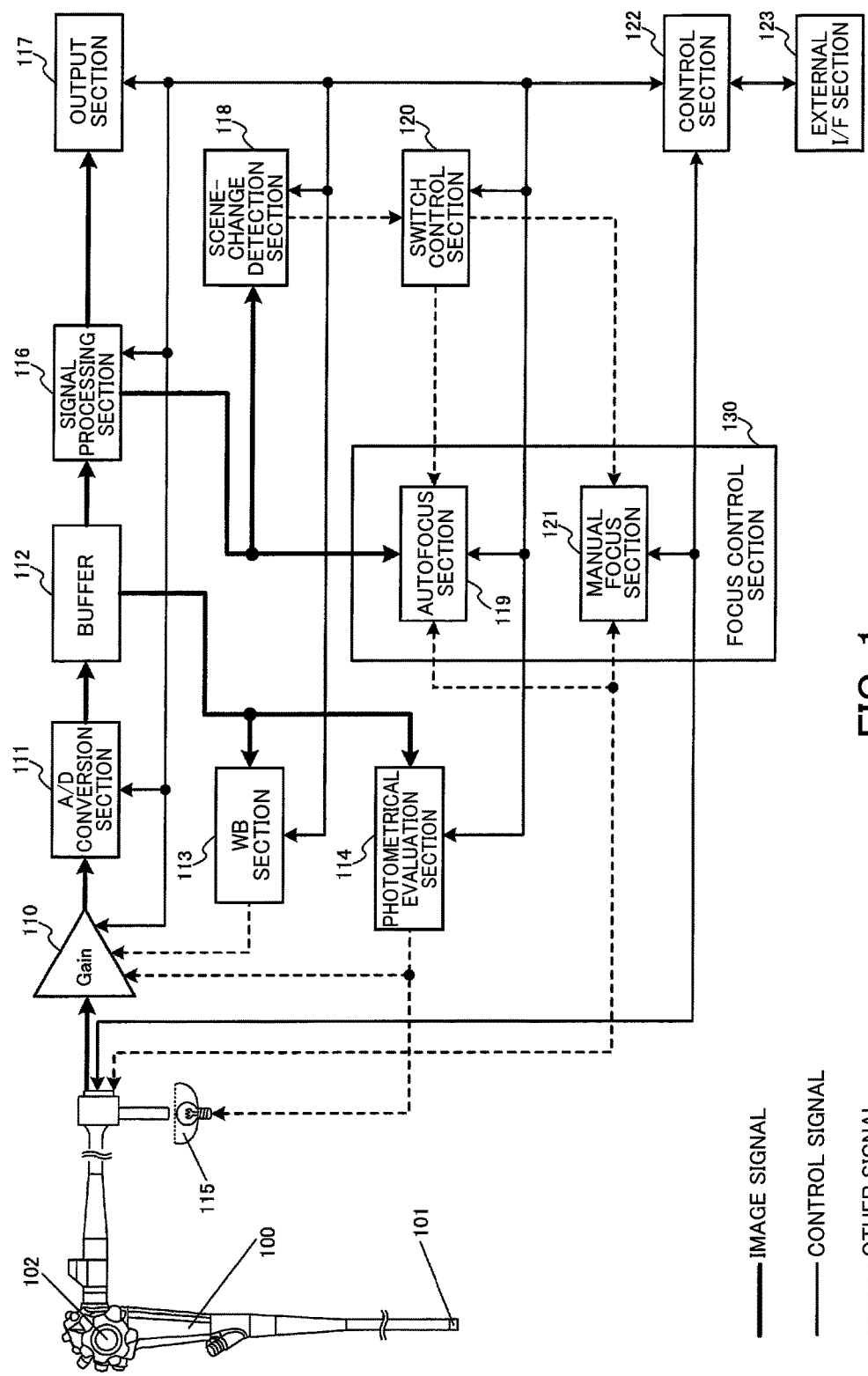
FIG. 1 illustrates a configuration example of an endoscope apparatus according to one embodiment of the invention.

According to one embodiment of the invention, there is provided an endoscope apparatus comprising:

a focus control section that performs a focus control process that controls a plurality of in-focus object plane positions by controlling an optical system, the plurality of in-focus object plane positions being set discretely;

a switch control section that switches the focus control process performed by the focus control section between an autofocus control process and a manual focus control process, the in-focus object plane position being automatically controlled when the focus control section performs the autofocus control process, and manually controlled when the focus control section performs the manual focus control process; and an operation section that is operated by a user, when the operation section has been operated by the user during a period in which the focus control section performs the autofocus control process, the switch control section switching the focus control process performed by the focus control section from the autofocus control process to the manual focus control process, and the focus control section moving the in-focus object plane position to an in-focus object plane position among the plurality of in-focus object plane positions that differs from the in-focus object plane position when the operation section has been operated by the user.

According to another embodiment of the invention, there is provided a method for controlling an endoscope apparatus that controls a plurality of in-focus object plane positions by controlling an optical system, the plurality of in-focus object plane positions being set discretely, the method comprising:

receiving an operation performed by a user;

switching a focus control process between an autofocus control process and a manual focus control process, and moving the in-focus object plane position based on the received operation performed by the user, the in-focus object plane position being automatically controlled when the autofocus control process is performed, and manually controlled when the manual focus control process is performed; and when the operation performed by the user has been received during a period in which the autofocus control process is performed, switching the focus control process from the autofocus control process to the manual focus control process, and moving the in-focus object plane position to an in-focus object plane position among the plurality of in-focus object plane positions that differs from the in-focus object plane position when the operation performed by the user has been received.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Method

A method used in connection with several exemplary embodiments of the invention is described below. In recent years, an endoscope apparatus has been used that can implement an autofocus (AF) control process (i.e., autofocus (AF) operation or autofocus (AF) function). The autofocus control process can reduce the burden imposed on the user (doctor) relating to the focus operation.

However, an image desired by the user may not be acquired even when the autofocus control process is performed. For example, when using a contrast AF method, it is difficult to accurately calculate the contrast value when only an image with a small amount of high-frequency component (e.g., edge component) is obtained. Even if the contrast value is appropriately calculated, an area other than the attention area is brought into focus when the attention area differs from the contrast value calculation area. When a plurality of attention areas are present at the near point and the far point, it is difficult to bring all of the attention areas into focus since the depth of field is shallow.

Therefore, it is indispensable to switch the focus control process between the autofocus control process and the manual focus control process. In this case, however, the burden imposed on the user increases. Specifically, when the user has determined that the desired object in the captured image is out of focus, the user performs a certain operation. When the endoscope apparatus does not have an autofocus function, the user may move the in-focus object plane position (i.e., the position of the object that is in focus (the details thereof are described later). When the endoscope apparatus has an autofocus function, the user also must take account of switching between the autofocus control process and the manual focus control process.

For example, when the autofocus control process is currently performed, and the desired object is out of focus, the user determines that the autofocus control process does not function effectively in the current situation, and switches the focus control process to the manual focus control process. When the manual focus control process is currently performed, and the desired object is out of focus, the user must determine whether to switch the focus control process to the autofocus control process, or move the in-focus object plane position without switching the focus control process to the autofocus control process. It is considered that the user basically switches the focus control process to the autofocus control process. However, when the user has switched the focus control process to the autofocus control process, and the autofocus control process has not functioned effectively, the user moves the in-focus object plane position without switching the focus control process to the autofocus control process, for example. Specifically, since the user must determine whether the autofocus control process or the manual focus control process is currently used, and remember the operation history, for example, the burden imposed on the user significantly increases.

JP-A-2009-142586 discloses an automatic switching technique that is implemented by the system. However, the switching technique disclosed in JP-A-2009-142586 is not satisfactory. The autofocus control process has superiority over the manual focus control process when it is desired to reduce the burden imposed on the user. According to the technique disclosed in JP-A-2009-142586, however, the manual focus control process may be used even when the autofocus control process will function effectively, and the user must perform a switching operation in order to utilize the autofocus control process to a maximum extent. Moreover, since the process that switches the focus control process between the autofocus control process and the manual focus control process, and the process that moves the in-focus object plane position during the manual focus control process are implemented by a different operation, the user must perform a complex operation.

In order to deal with the above problems, several embodiments of the invention propose a method that implements a focus control process that reduces the burden imposed on the user by appropriately combining a process that automatically switches the focus control process, a process that switches the focus control process based on an operation performed by the user, and a process that moves the in-focus object plane position.

Specifically, when the user has performed a given operation (single operation in a narrow sense (the details thereof are described later)) when the autofocus control process is performed, the focus control process is switched to the manual focus control process, and the in-focus object plane position is moved. The in-focus object plane position is moved by an operation that is identical with the given operation when the manual focus control process is performed. When a scene change has been detected when the manual focus control process is performed, for example, the system switches the focus control process to the autofocus control process.

When using the above method, only one type of operation is required for the user relating to the focus control process. When the user has performed the operation once, the in-focus object plane position is moved, and the focus control process is optionally switched to the manual focus control process. Specifically, the user need not determine whether the autofocus control process or the manual focus control process is currently performed, and it suffices that the user perform the given operation when the user has determined that the desired object is out of focus. Since the user need not determine whether the autofocus control process or the manual focus control process is currently performed, and remember the operation history, for example, it is possible to reduce the burden imposed on the user. Moreover, since the configuration of the operation section can be simplified, the burden imposed on the user can be further reduced.

The autofocus control process is resumed when a scene change has been detected when the manual focus control process is performed. When a scene change (e.g., object (imaging target)) has occurred, the autofocus control process may function effectively even when the autofocus control process has not functioned effectively before the scene change has occurred. Specifically, the focus control process is positively switched to the autofocus control process although it is unclear whether the autofocus control process functions effectively after the scene change has occurred. This increases the probability that the autofocus control process is performed, and reduce the burden imposed on the user. When the autofocus control process does not function effectively after the scene change has occurred, it suffices that the user perform the given operation. This does not increase the burden imposed on the user.

A first embodiment and a second embodiment of the invention are described below. The first embodiment and the second embodiment have a similar basic configuration. In the first embodiment, a contrast AF method is used as the autofocus method, and a scene change is used as the condition whereby the focus control process is switched from the manual focus control process to the autofocus control process. In the second embodiment, a phase detection AF method is used as the autofocus method, and the elapsed time is also used as the condition whereby the focus control process is switched from the manual focus control process to the autofocus control process in addition to a scene change. Note that an arbitrary autofocus method and an arbitrary autofocus switching condition may be combined.

2. First Embodiment

FIG. 1 illustrates a configuration example of an endoscope apparatus according to the first embodiment. As illustrated in FIG. 1, a scope 100 included in the endoscope apparatus includes an end section 101 that is inserted into a living body, and an operation section 102 that allows the user to perform an angular operation on the end section 101, and perform a focus control operation.

Figure 2A:
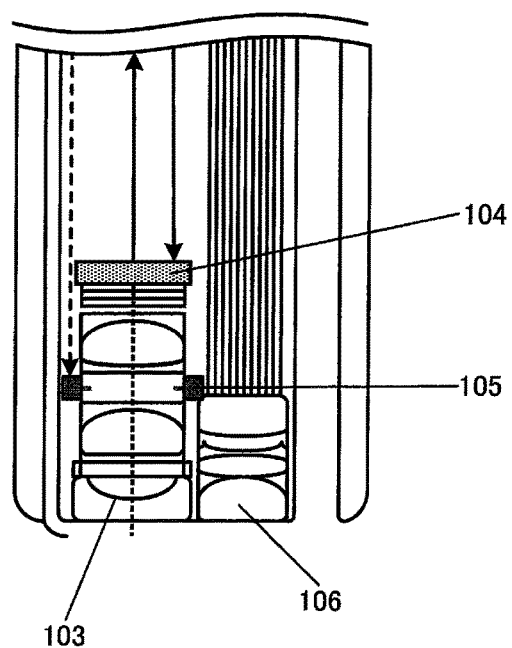
FIG. 2A illustrates a configuration example of an end section.

FIG. 2A illustrates a detailed configuration example of the end section 101. Image signals generated through a lens system 103 and a CCD 104 provided in the end section 101 are output from the CCD 104. The lens system 103 is configured to allow a focus adjustment, and a lens driver section 105 (e.g., stepping motor) for adjusting the focus of the lens system 103 is provided in the end section 101. An illumination lens system 106 that emits illumination light is provided in the vicinity of the lens system 103.

Figure 2B:
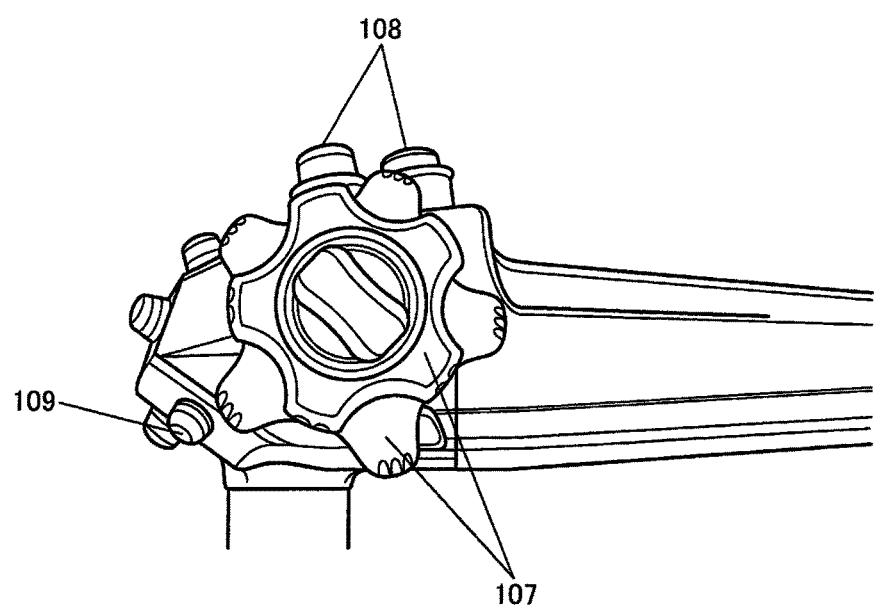
FIG. 2B illustrates a configuration example of an operation section.

FIG. 2B illustrates a detailed configuration example of the operation section 102. The operation section 102 includes an angular operation section 107 for performing an angular operation on the end section 101, an air/water supply switch 108 for controlling air/water supply, and a focus switch 109 for performing a focus control operation.

The endoscope apparatus according to the first embodiment includes each section illustrated in FIG. 1 in addition to the scope 100. Note that the configuration of the endoscope apparatus is not limited to the configuration illustrated in FIG. 1. Various modifications may be made, such as omitting some of the elements illustrated in FIG. 1 or adding other elements. The image signals output from the CCD 104 are amplified by a Gain 110, and converted into digital signals through an A/D conversion section 111. The image signals output from the A/D conversion section 111 are transmitted to a WB section 113, a photometrical evaluation section 114, and a signal processing section 116 through a buffer 112. The WB section 113 is connected to the Gain 110, and the photometrical evaluation section 114 is connected to an illumination light source 115 and the Gain 110. Illumination light emitted from the illumination light source 115 is guided to the illumination lens system 106 provided in the end section 101 of the scope 100 through an optical fiber, and applied to an object. The signal processing section 116 is connected to an output section 117, a scene-change detection section 118, and an autofocus section 119. The scene-change detection section 118 is connected to a switch control section 120, and the switch control section 120 is connected to the autofocus section 119 and a manual focus section 121. The autofocus section 119 and the manual focus section 121 are bidirectionally connected to the lens driver section 105. Note that the endoscope apparatus may include a focus control section 130, and the focus control section 130 may include the autofocus section 119 and the manual focus section 121.

A control section 122 that is implemented by a microcomputer or the like is bidirectionally connected to the CCD 104, the angular operation section 107, the air/water supply switch 108, the focus switch 109, the Gain 110, the A/D conversion section 111, the WB section 113, the photometrical evaluation section 114, the signal processing section 116, the output section 117, the scene-change detection section 118, the autofocus section 119, the switch control section 120, and the manual focus section 121. The control section 122 is also bidirectionally connected to an external I/F section 123 that includes a power switch, and an imaging mode setting (switching) interface.

The flow of the process is described below with reference to FIGS. 1, 2A, and 2B. The endoscope apparatus is turned ON, and the imaging conditions are set using the external I/F section 123. The image signals generated through the lens system 103 and the CCD 104 are successively output as analog signals at given time intervals. The following description is given taking an example in which the given time interval is 1/60th of a second, and the CCD 104 is a single-chip CCD in which a Bayer primary color filter array is disposed on the front side. A xenon light source may be used as the illumination light source 115.

The analog signal is amplified by the Gain 110 by a given amplification factor, converted into a digital signal through the A/D conversion section 111, and transmitted to the buffer 112. The buffer 112 can store (record) the image signals corresponding to one image, and the image signals are overwritten with new image signals each time one image has been captured. The image signals stored in the buffer 112 are intermittently transmitted to the WB section 113 and the photometrical evaluation section 114 at given time intervals under control of the control section 122. The WB section 113 integrates signals at a given level corresponding to each color signal that corresponds to each color filter to calculate a white balance coefficient. The WB section 113 transmits the white balance coefficient to the Gain 110. The Gain 110 multiplies each color signal by a different gain to implement a white balance process. The photometrical evaluation section 114 controls the amplification factor of the Gain 110, the intensity of light emitted from the illumination light source 115, and the like so that a correct exposure is achieved.

The signal processing section 116 reads the image signals, and performs an interpolation process, a grayscale process, and the like on the image signals under control of the control section 122. The resulting image signals are transmitted to the output section 117. The output section 117 may be a display section such as a liquid crystal display or an organic EL display. In this case, the output section 117 sequentially displays the image signals (captured image) transmitted from the signal processing section 116. Note that the output section 117 may sequentially store the image signals (captured image) in a recording medium such as a hard disk or a memory card.

The image signals output from the signal processing section 116 are also transmitted to the scene-change detection section 118 and the autofocus section 119. The scene-change detection section 118 reads the image signals output from the signal processing section 116 at given time intervals (e.g., at intervals of 1/60th of a second), and calculates the amount of change between the consecutive image signals under control of the control section 122. For example, the sum of the absolute values of the differences between brightness signals is used as the amount of change. The scene-change detection section 118 determines that a scene change has been detected when the amount of change has exceeded a given threshold value. The scene-change detection result is transmitted to the switch control section 120.

The switch control section 120 switches the focus control process performed by the focus control section 130 based on a control signal output from a focus switch 109 through the control section 122, and the scene-change detection result output from the scene-change detection section 118. Specifically, the switch control section 120 controls the operation (start/stop) of the autofocus section 119 and the manual focus section 121. The autofocus section 119 and the manual focus section 121 are controlled to operate exclusively. The autofocus section 119 and the manual focus section 121 generate a drive signal for driving the lens driver section 105 to adjust the focus of the lens system 103.

Figure 3A:
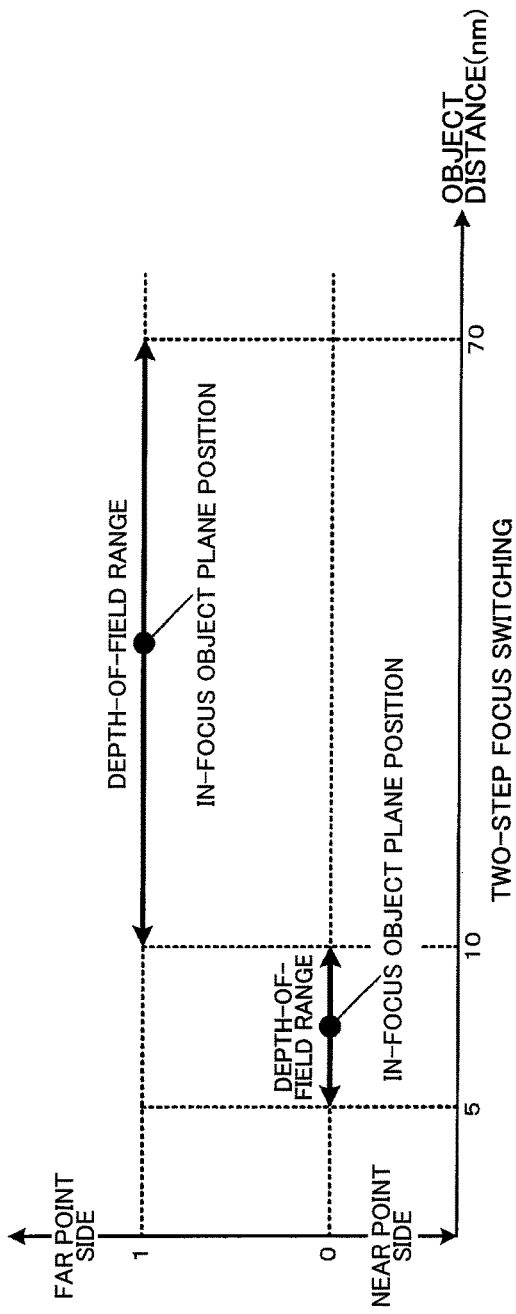
FIGS. 3A and 3B are views illustrating the relationship between an in-focus object plane position and a depth-of-field range when implementing a discrete focus control process.
Figure 3B:
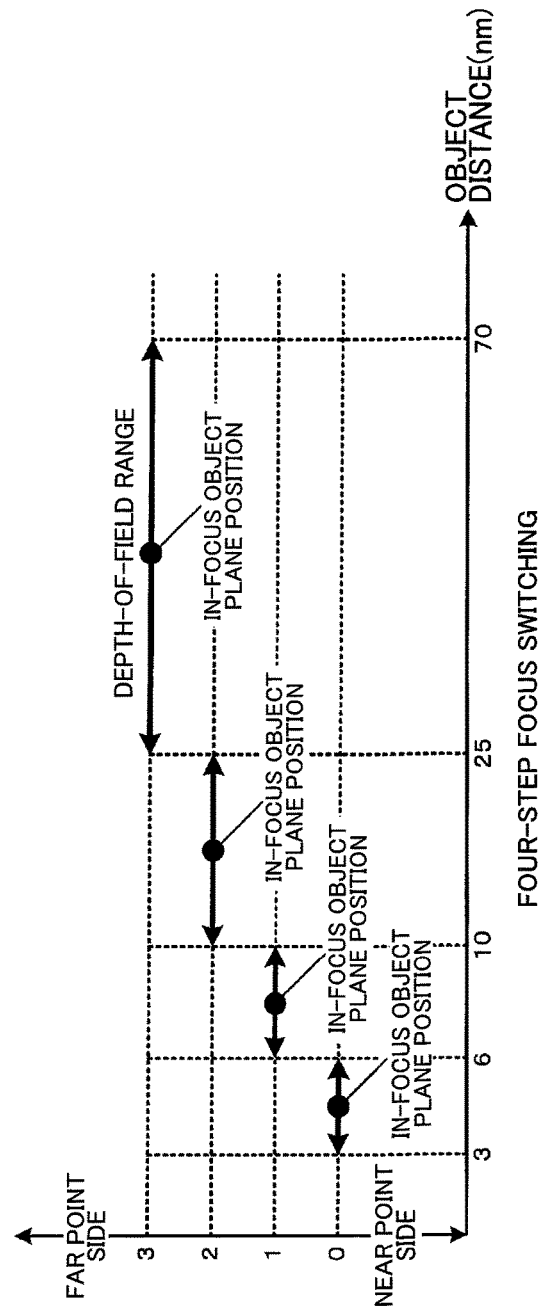

FIG. 3A is a view illustrating the in-focus object plane position and the depth-of-field range according to the first embodiment. A deep focus range of about 5 to 70 mm is normally required for an endoscope. In the first embodiment, a two-step focus switching imaging system may be used that requires a two-step focus switching operation in order to cover the deep focus range. In this case, the drive signal generated by the autofocus section 119 or the manual focus section 121 designates 0 (near point-side position) or 1 (far point-side position). The number of steps of the in-focus object plane position required to cover the deep focus range differs depending on the image sensor, the aperture, the optical system, and the like of the imaging system. FIG. 3B illustrates an example of a four-step focus switching imaging system that requires a four-step focus switching operation in order to cover the deep focus range. In this case, the drive signal generated by the autofocus section 119 or the manual focus section 121 designates one of 0 to 3.

Figure 4:
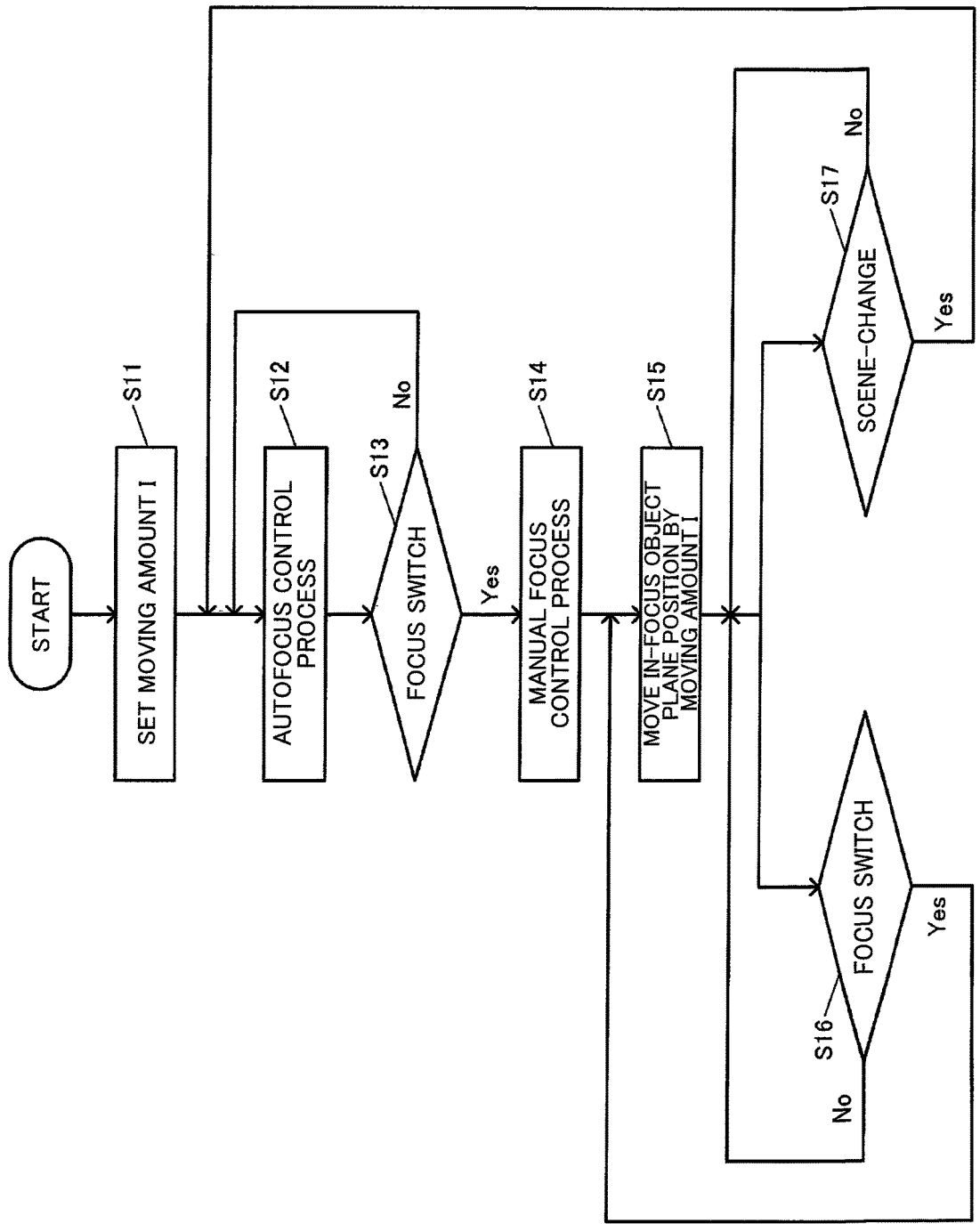
FIG. 4 is a flowchart illustrating a process according to one embodiment of the invention.

FIG. 4 is a flowchart illustrating a switch control process (i.e., a focus control process that switches a focus control process performed by the focus control section 130 between a autofocus control process and a manual focus control process) performed by the switch control section 120, and the focus control process performed by the focus control section 130. In the first embodiment, the switch control process is always performed when power is being supplied, and the process illustrated in FIG. 4 starts when power has been supplied. The process is terminated when power supply has been stopped. Since power supply may be stopped at an arbitrary timing, termination of the process is not illustrated in FIG. 4. Note that the switch control process need not always be performed over a period in which power is supplied. A period may be provided in which the switch control process is not performed even when power is supplied.

When power has been supplied using the external I/F section 123, the control section 122 transmits a signal relating to the startup of the endoscope apparatus to the switch control section 120. The switch control section 120 sets a moving amount I for the manual focus section 121 (S11). Note that the moving amount I represents the amount of change in the in-focus object plane position. The term "in-focus object plane position" used herein refers to the position of the object at which the object is brought into focus when the optical system is set to a certain state. In the first embodiment, the state of the optical system is determined by the position of the focus lens. Therefore, the in-focus object plane position has a correlation with the position of the focus lens. When the in-focus object plane position can be successively controlled, the moving amount I may be the amount of change in the in-focus object plane position (e.g., movement in an amount of I mm). Since the discrete N-step focus switching operation (see FIGS. 3A and 3B) may be employed in the first embodiment, the moving amount I may represent a change in ID that is sequentially assigned to each in-focus object plane position (or each focus lens position). For example, when the moving amount I is set to 1, the manual focus section performs the focus control process that moves the in-focus object plane position to the adjacent position. The moving amount I may be set to a fixed value, or the user may set the moving amount I to an arbitrary value using the external I/F section 123.

The switch control section 120 then outputs a control signal that causes the autofocus section 119 to start operation. Specifically, the autofocus section 119 operates when the endoscope apparatus has started operation (S12). The user maintains the above state as long as the autofocus control process functions successfully. However, a scene (situation) may occur in which the desired position cannot be brought into focus by the autofocus control process (e.g., when a plurality of attention areas are present at the near point and the far point, or when a single attention area is present over a wide range from the near point to the far point). In this case, it is considered that the user presses the focus switch 109 provided to the operation section 102. Therefore, whether or not the focus switch 109 has been pressed is determined (S13). In the first embodiment, a one-way switch may be used as the focus switch 109.

When the focus switch 109 has been pressed (Yes in S13), the corresponding control signal is transmitted to the switch control section 120 through the control section 122. When the switch control section 120 has received the control signal (that indicates that the focus switch 109 has been pressed) from the control section 122, the switch control section 120 causes the autofocus section 119 to stop operation, and causes the manual focus section 121 to start operation (S14). The switch control section 120 outputs a control signal that instructs the manual focus section 121 to move the in-focus object plane position by the moving amount I.

The manual focus section 121 moves the in-focus object plane position by the moving amount I (S15). In the first embodiment, the two-step focus switching imaging system illustrated in FIG. 3A may be used, and the moving amount I may be set to 1. When the current in-focus object plane position (or the corresponding focus lens position) is situated at the near point-side position (ID=0), the manual focus section 121 moves the in-focus object plane position to the far point-side position at which ID=1 is satisfied since "0+moving amount I=1". When the current in-focus object plane position is situated at the far point-side position (ID=1), the number of steps of the in-focus object plane positions is exceeded since "1+moving amount I=2". In this case, the sign of the moving amount I is reversed (i.e., I=−1). Therefore, when the current in-focus object plane position is situated at the far point-side position (ID=1), the manual focus section 121 moves the in-focus object plane position to the near point-side position since "1+moving amount I=0". The sign of the moving amount I may also be reversed when the value calculated as described above falls below 0.

Since the focus switch 109 is pressed when the desired position cannot be brought into focus by the autofocus control process, the desired position can be brought into focus by moving the in-focus object plane position to another position. Since such a scene is determined to be a scene in which the autofocus control process does not function successfully, a focus control process that is desired for the user cannot be implemented if the autofocus control process is continuously performed after moving the in-focus object plane position. Therefore, when it has been determined that the focus switch 109 has been pressed in the step S13, the focus control process is switched to the manual focus control process (S14), and the in-focus object plane position is moved (S15).

Even when the focus control process has been switched to the manual focus control process in the step S14, and the manual focus control process is being performed, the user may press the focus switch 109 when the user desires to move the in-focus object plane position to another position. Therefore, whether or not the focus switch 109 has been pressed is determined (S16), and the in-focus object plane position is moved by the moving amount I through the manual focus control process when the focus switch 109 has been pressed (S15). When the focus switch 109 has not been pressed, the current in-focus object plane position is maintained through the manual focus control process.

When the manual focus control process is performed, whether or not a scene change has been detected is also determined (S17). When the user has completed observation/diagnosis in the current scene, and started observation/diagnosis in another scene, the scene-change detection section 118 detects the scene change, and transmits the detection result to the switch control section 120 (i.e., Yes in S17). When the switch control section 120 has received a control signal relating to detection of a scene change from the scene-change detection section 118, the switch control section 120 causes the manual focus section 121 to stop operation, and causes the autofocus section 119 to start operation (S12). When a scene change has not been detected (No in S17), the current in-focus object plane position is maintained through the manual focus control process.

Figure 5:
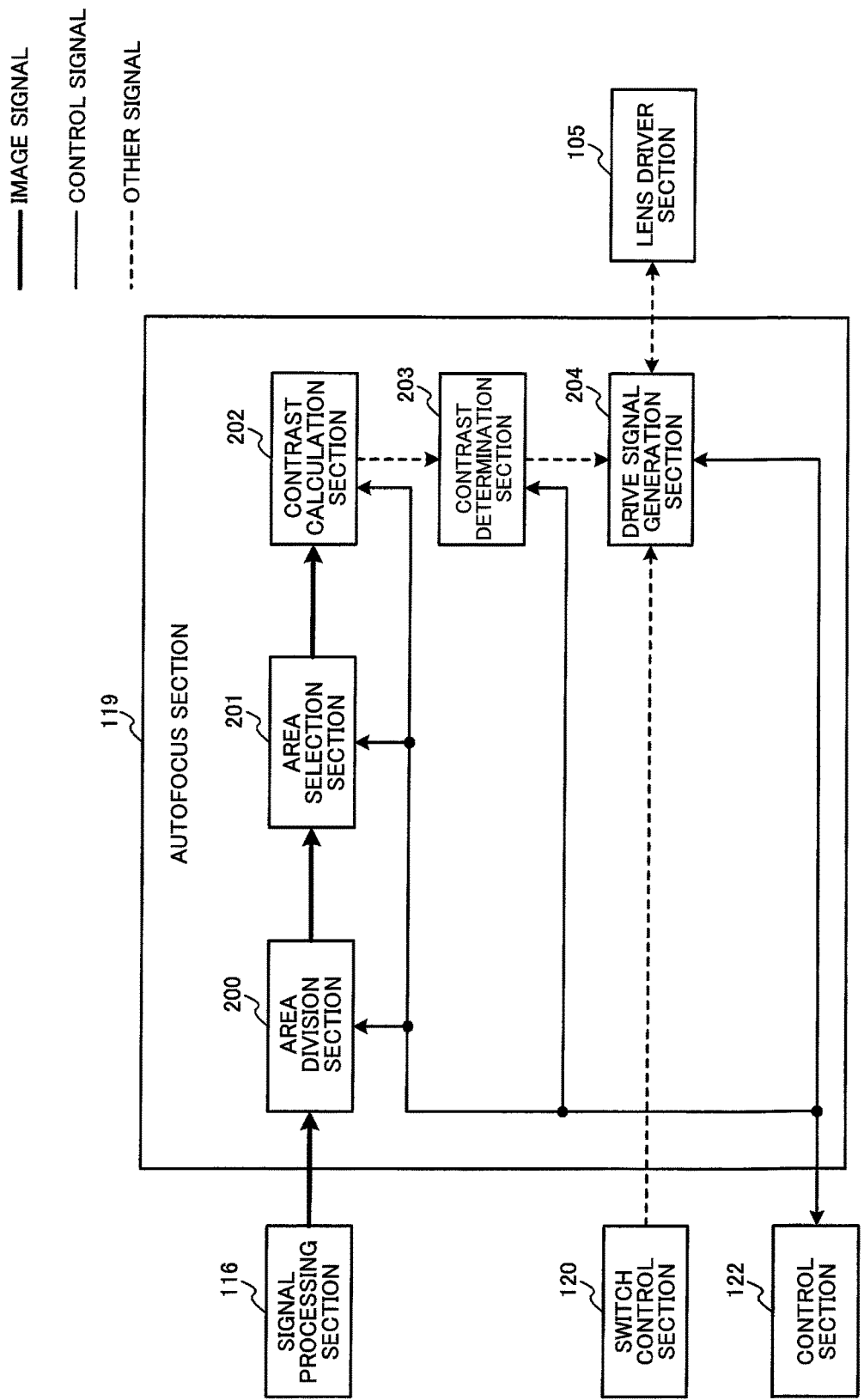
FIG. 5 illustrates a configuration example of an autofocus section.

FIG. 5 illustrates a detailed configuration example of the autofocus section 119. The autofocus section 119 includes an area division section 200, an area selection section 201, a contrast calculation section 202, a contrast determination section 203, and a drive signal generation section 204. The signal processing section 116 is connected to the contrast calculation section 202 through the area division section 200 and the area selection section 201. The contrast calculation section 202 is connected to the drive signal generation section 204 through the contrast determination section 203. The drive signal generation section 204 is bidirectionally connected to the lens driver section 105. The switch control section 120 is connected to the drive signal generation section 204. The control section 122 is bidirectionally connected to the area division section 200, the area selection section 201, the contrast calculation section 202, the contrast determination section 203, and the drive signal generation section 204.

The autofocus section 119 according to the first embodiment utilizes the area division/contrast method disclosed in JP-A-2011-139760, for example. The image signals (captured image) output from the signal processing section 116 are transmitted to the area division section 200 under control of the control section 122. The area division section 200 divides the image signals into a plurality of block areas having a given size, and transmits information about each block area to the area selection section 201 under control of the control section 122.

The area selection section 201 selects the focus target block area based on the brightness distribution of each block area, and transmits information about the selected block area to the contrast calculation section 202 under control of the control section 122. The contrast calculation section 202 calculates the contrast value of the selected block area, and transmits the calculated contrast value to the contrast determination section 203 under control of the control section 122.

The contrast determination section 203 compares the contrast value transmitted from the contrast calculation section 202 with a given threshold value under control of the control section 122. The contrast determination section 203 determines that the block area is out of focus when the contrast value is smaller than the threshold value, and determines that the block area is in focus when the contrast value is larger than the threshold value. The contrast determination section 203 transmits a control signal that instructs the drive signal generation section 204 to output a drive signal only when it has been determined that the block area is out of focus. The drive signal generation section 204 checks the control signals from the switch control section 120 and the contrast determination section 203 under control of the control section 122. The drive signal generation section 204 transmits the drive signal for moving the in-focus object plane position to the lens driver section 105 when the control signal that causes the autofocus section 119 to start operation has been output from the switch control section 120, and the control signal has been output from the contrast determination section 203. When the two-step focus switching imaging system illustrated in FIG. 3A is used, the drive signal generation section 204 transmits the drive signal for moving the in-focus object plane position to a position differing from the current in-focus object plane position. Note that a position signal that indicates the current in-focus object plane position is always transmitted from the lens driver section 105.

Although a configuration example that implements the autofocus control process that utilizes the area division/contrast method has been described above, another configuration may also be employed. For example, an autofocus control process that utilizes a phase detection method or the like may also be employed.

Figure 6:
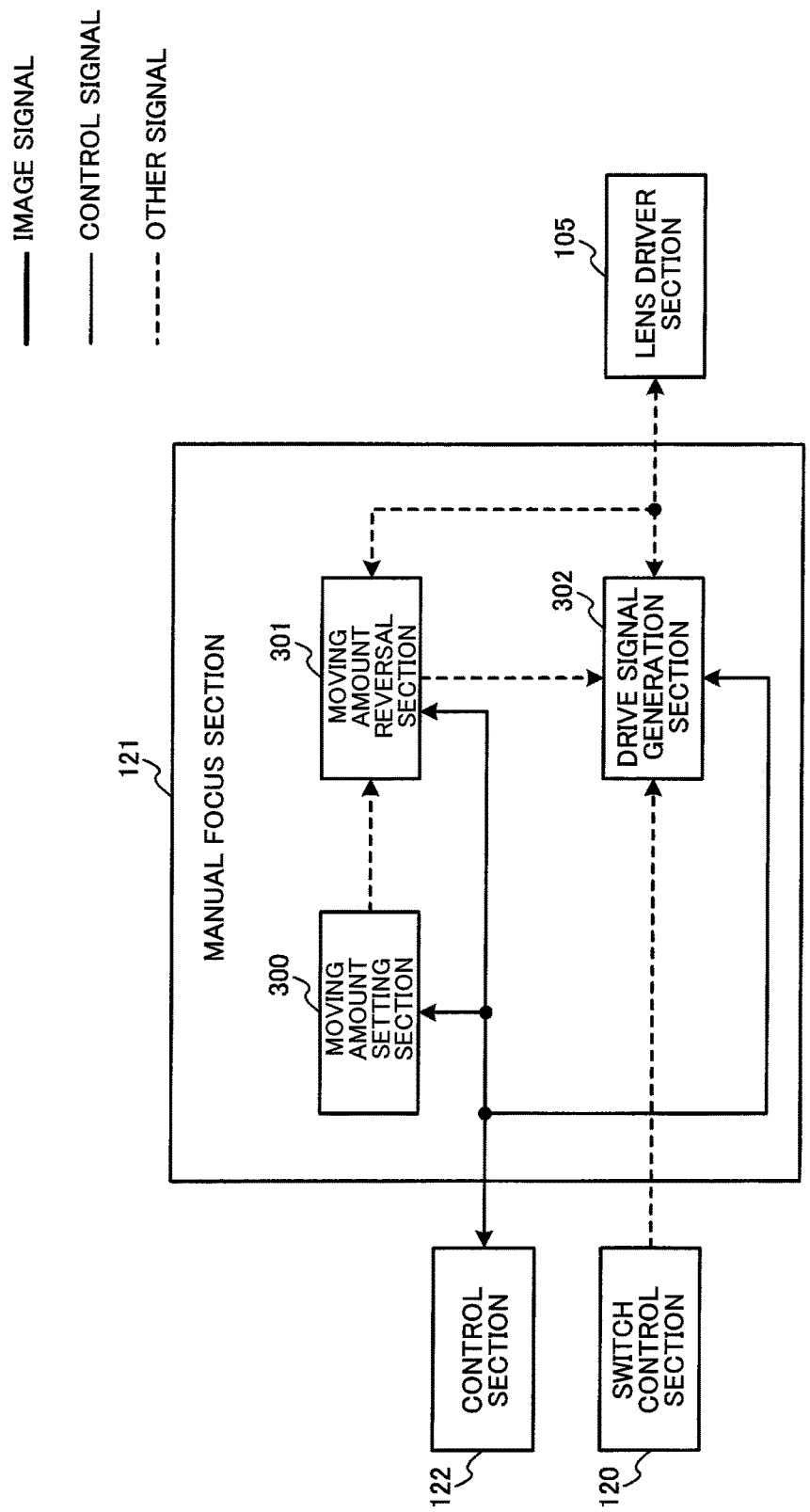
FIG. 6 illustrates a configuration example of a manual focus section.

FIG. 6 illustrates a detailed configuration example of the manual focus section 121. The manual focus section 121 includes a moving amount setting section 300, a moving amount reversal section 301, and a drive signal generation section 302. The moving amount setting section 300 is connected to the moving amount reversal section 301, and the moving amount reversal section 301 is connected to the drive signal generation section 302. The moving amount reversal section 301 and the drive signal generation section 302 are bidirectionally connected to the lens driver section 105. The switch control section 120 is connected to the drive signal generation section 302. The control section 122 is bidirectionally connected to the moving amount setting section 300, the moving amount reversal section 301, and the drive signal generation section 302.

The moving amount setting section 300 sets the moving amount I by which the in-focus object plane position of the optical system is moved when the signal relating to startup of the endoscope apparatus has been received from the switch control section 120. In the first embodiment, the moving amount I is set to 1. The moving amount I may be set to a fixed value, or the user may set the moving amount I to an arbitrary value using the external I/F section 123. The moving amount I set by the moving amount setting section 300 is transmitted to the moving amount reversal section 301.

The moving amount reversal section 301 determines whether or not the allowable range is exceeded when the in-focus object plane position is moved from the current position by the moving amount I, and reverses the sign of the moving amount I when it has been determined that the allowable range is exceeded, under control of the control section 122. Specifically, the moving amount I may be added to the ID that indicates the current in-focus object plane position, and the sign of the moving amount I may be reversed when the resulting value falls below or exceeds the number of steps of the in-focus object plane position. When the two-step focus switching imaging system illustrated in FIG. 3A is used, the sign of the moving amount I is reversed when the resulting value falls below 0, or exceeds 1. Note that the position signal that indicates the current in-focus object plane position is always transmitted from the lens driver section 105. The moving amount I subjected to the above process is transmitted to the drive signal generation section 302.

The drive signal generation section 302 checks the control signal output from the focus switch 109 through the control section 122, and the control signal that is output from the switch control section 120 and causes the manual focus section 121 to start operation. When the control signal output from the focus switch 109 or the control signal output from the switch control section 120 has been received, the drive signal generation section 302 transmits a drive signal that causes the lens driver section 105 to move the in-focus object plane position by the moving amount I output from the moving amount reversal section 301.

The above configuration makes it possible to provide an endoscope apparatus that is configured to normally perform the autofocus control process, and perform the manual focus control process when the user has operated a one-way switch when the desired position cannot be brought into focus by the autofocus control process. The endoscope apparatus according to the first embodiment is configured to perform the autofocus control process without receiving an instruction from the user when a scene change has occurred during the manual focus control process. Therefore, it is possible to provide an endoscope apparatus with good operability that allows the user to adjust the in-focus object plane position by merely operating a one-way switch without taking account of switching between the autofocus control process and the manual focus control process.

3. Second Embodiment

Figure 7:
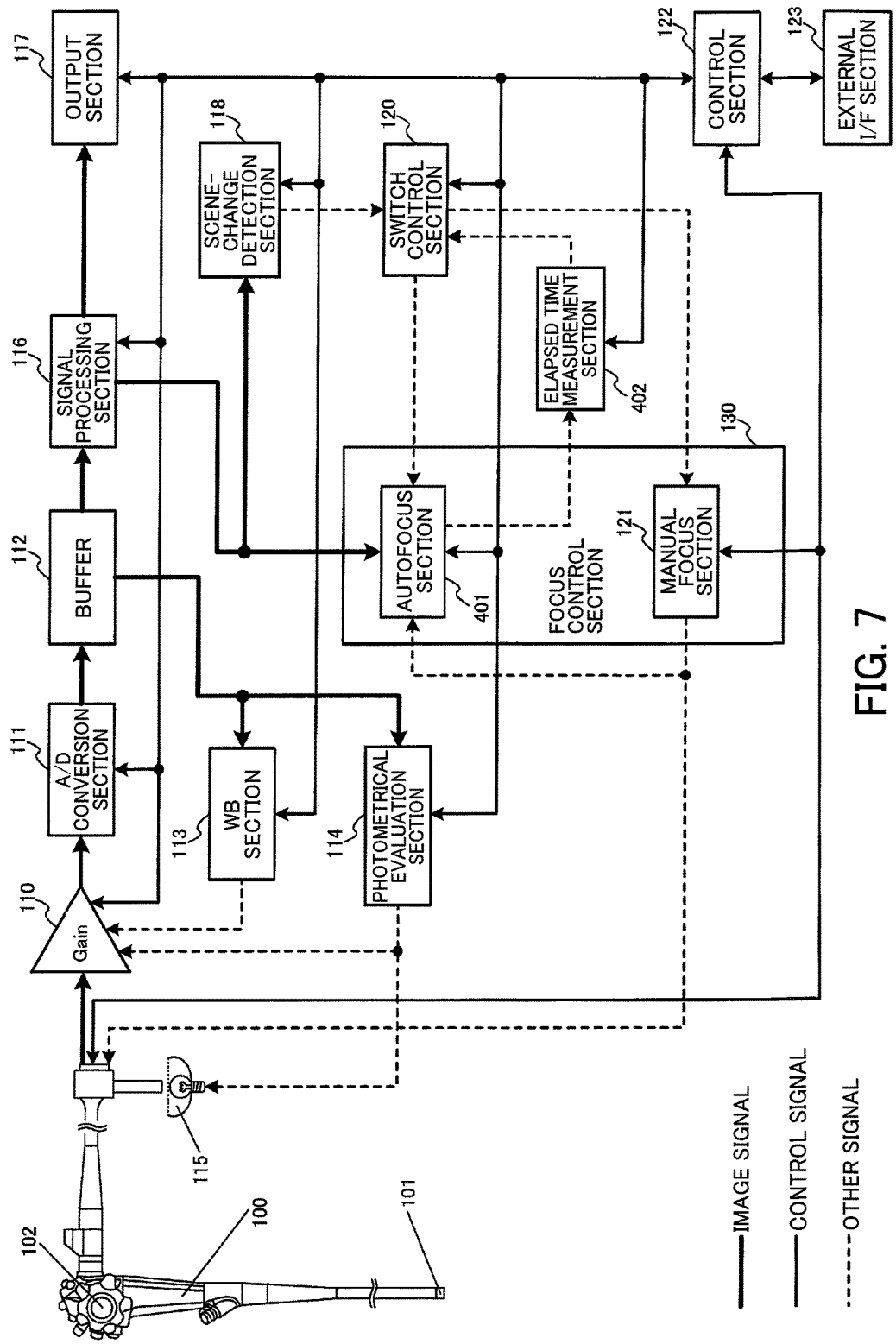
FIG. 7 illustrates another configuration example of an endoscope apparatus according to one embodiment of the invention.
Figure 8:
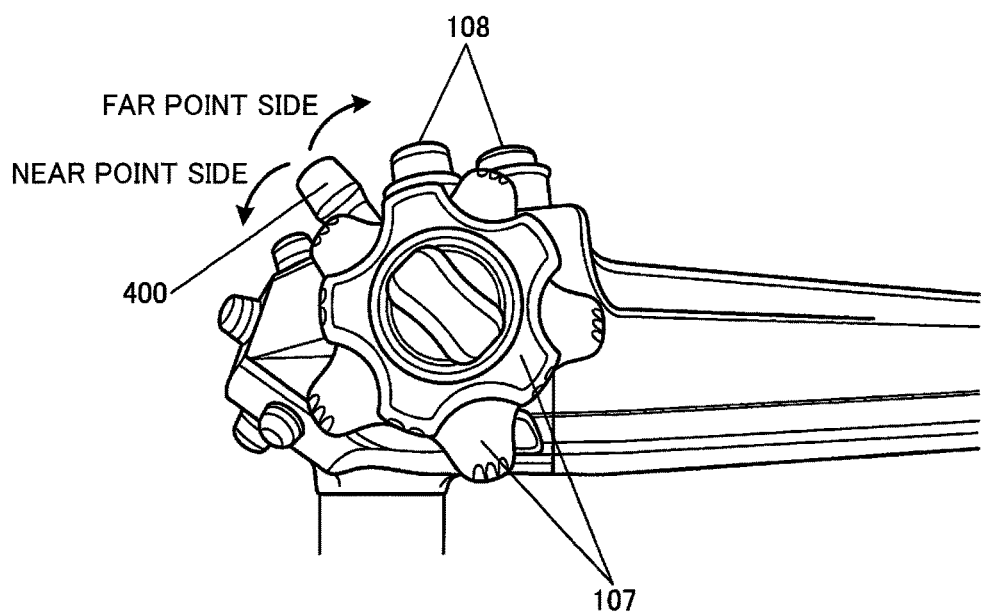
FIG. 8 illustrates another configuration example of an operation section.

FIG. 7 illustrates a configuration example of an endoscope apparatus according to the second embodiment. FIG. 8 illustrates a detailed configuration example of an operation section 102 included in a scope 100. As illustrated in FIG. 8, the operation section 102 according to the second embodiment is configured in the same manner as the operation section 102 according to the first embodiment, except that a focus switch 400 (two-way switch) is provided instead of the focus switch 109 (one-way switch) (see FIG. 1). As illustrated in FIG. 7, an autofocus section 401 that utilizes a phase detection method is provided instead of the autofocus section 119 that utilizes a contrast method, and an elapsed time measurement section 402 is additionally provided. The basic configuration according to the second embodiment is similar to that according to the first embodiment. The same elements as those described above in connection with the first embodiment are respectively indicated by the same name and the same reference number as those used in connection with the first embodiment. The following description focuses on the differences from the first embodiment.

FIG. 8 illustrates a detailed configuration example of the operation section 102 according to the second embodiment. The operation section 102 includes the angular operation section 107 for performing an angular operation on the end section 101, the air/water supply switch 108 for controlling air/water supply, and the focus switch 400 for performing a focus control operation.

As illustrated in FIG. 7, the signal processing section 116 is connected to the output section 117, the scene-change detection section 118, and the autofocus section 401. The autofocus section 401 is bidirectionally connected to the lens driver section 105. The autofocus section 401 is also connected to the elapsed time measurement section 402. The elapsed time measurement section 402 is connected to the switch control section 120. The control section 122 is bidirectionally connected to the focus switch 400, the autofocus section 401, and the elapsed time measurement section 402.

The flow of the process according to the second embodiment is described below with reference to FIGS. 7 and 8. The flow of the process according to the second embodiment is basically the same as the flow of the process according to the first embodiment. The following description focuses on the differences from the first embodiment.

The switch control section 120 controls the operation (start/stop) of the autofocus section 401 and the manual focus section 121 based on a control signal output from the focus switch 400 and acquired through the control section 122, the scene-change detection result acquired from the scene-change detection section 118, and an elapsed time acquired from the elapsed time measurement section 402. The autofocus section 401 generates a drive signal for driving the lens driver section 105 to adjust the focus of the lens system 103. When the autofocus section 401 has started operation under control of the switch control section 120, the autofocus section 401 transmits a signal (that indicates that the autofocus section 401 operates) to the elapsed time measurement section 402 during a period in which the autofocus section 401 operates. The elapsed time measurement section 402 does not perform time measurement when the autofocus section 401 operates, and starts time measurement when the autofocus section 401 has stopped operation (i.e., has stopped transmitting the above signal). The elapsed time measurement section 402 continuously transmits the measured time to the switch control section 120. Note that the measured time is initialized to 0 when the autofocus section 401 has started operation again. In the second embodiment, a four-step focus switching imaging system may be used that requires a four-step focus switching operation in order to cover the deep focus range (see FIG. 3B).

Figure 9:
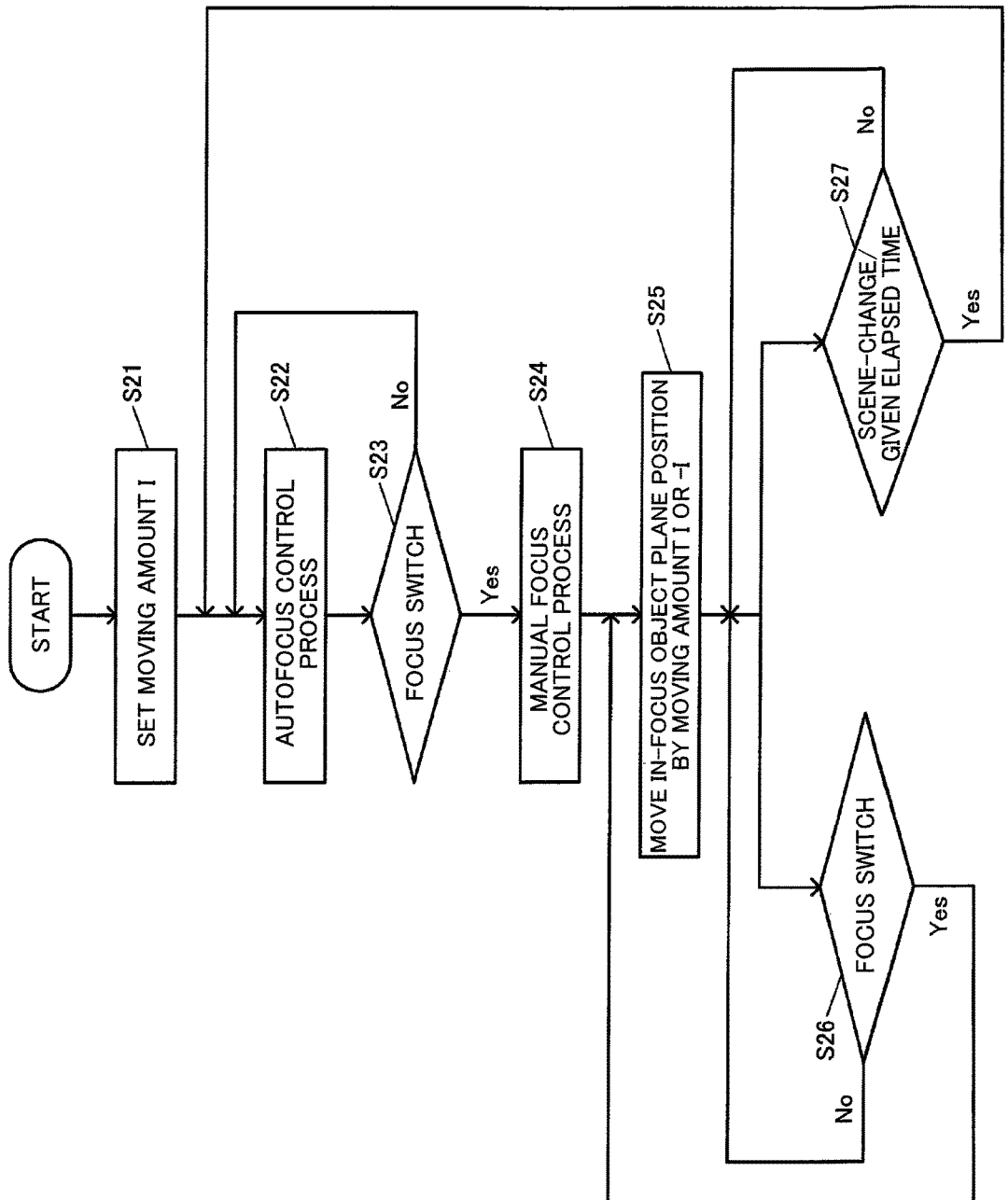
FIG. 9 is another flowchart illustrating a process according to one embodiment of the invention.

FIG. 9 is a flowchart illustrating the switch control process performed by the switch control section 120, and the focus control process performed by the focus control section 130.

The steps S21 and S22 in FIG. 9 are the same as the steps S11 and S12 in FIG. 4, and description thereof is omitted. In the step S23, whether or not the user has operated the focus switch 400 provided to the operation section 102 is determined. Note that the focus switch 400 is a two-way switch, differing from the first embodiment. The focus switch 400 generates a control signal that moves the in-focus object plane position toward the near point when the focus switch 400 has been pulled forward, and generates a control signal that moves the in-focus object plane position toward the far point when the focus switch 400 has been pushed backward. The control signal is transmitted to the switch control section 120 through the control section 122.

When the switch control section 120 has received the control signal (that indicates that the focus switch 400 has been operated) from the control section 122, the switch control section 120 causes the autofocus section 401 to stop operation, and causes the manual focus section 121 to start operation (S24). The switch control section 120 outputs the control signal that instructs the manual focus section 121 to move the in-focus object plane position by the moving amount I or −I.

The manual focus section 121 moves the in-focus object plane position by the moving amount I or −I based on the control signal output from the switch control section 120 (S25). In the second embodiment, the four-step focus switching imaging system illustrated in FIG. 3B may be used, and the moving amount I may be set to 1. The moving amount is −I when the focus switch 400 has been pulled forward since the in-focus object plane position is moved toward the near point. The moving amount is I when the focus switch 400 has been pushed backward since the in-focus object plane position is moved toward the far point. When the value calculated as described above exceeds the number (3) of steps of the in-focus object plane position, or falls below 0, the sign of the moving amount I is reversed. In this case, the in-focus object plane position is moved toward the near point (far point) due to the operation performed by the user who desires to move the in-focus object plane position toward the far point (near point). Since the user may be confused by such a situation, the sign of the moving amount I need not necessarily be reversed.

Even when the focus control process has been switched to the manual focus control process in the step S24, and the manual focus control process is being performed, the user may operate the focus switch 400 when the user desires to move the in-focus object plane position to another position. Therefore, whether or not the focus switch 400 has been operated is determined (S26), and the in-focus object plane position is moved by the moving amount I or −I when the focus switch 400 has been operated (S25). When the focus switch 400 has not been operated, the current in-focus object plane position is maintained through the manual focus control process.

When the manual focus control process is performed, whether or not a scene change has been detected, and whether or not a given time has elapsed are also determined (S27). When the user has completed observation/diagnosis in the current scene, and started observation/diagnosis in another scene, the scene-change detection section 118 detects the scene change, and transmits the detection result to the switch control section 120. The elapsed time measurement section 402 transmits the elapsed time after the autofocus section 401 has stopped operation to the switch control section 120. The switch control section 120 determines whether or not the scene-change detection section 118 has transmitted the control signal relating to detection of a scene change, and whether or not the elapsed time after the autofocus section 401 has stopped operation has exceeded a given time (S27). When the determination result in the step S27 is Yes, the switch control section 120 causes the manual focus section 121 to stop operation, and causes the autofocus section 401 to start operation (S22). When the determination result in the step S27 is No, the current in-focus object plane position is maintained through the manual focus control process.

Figure 10:
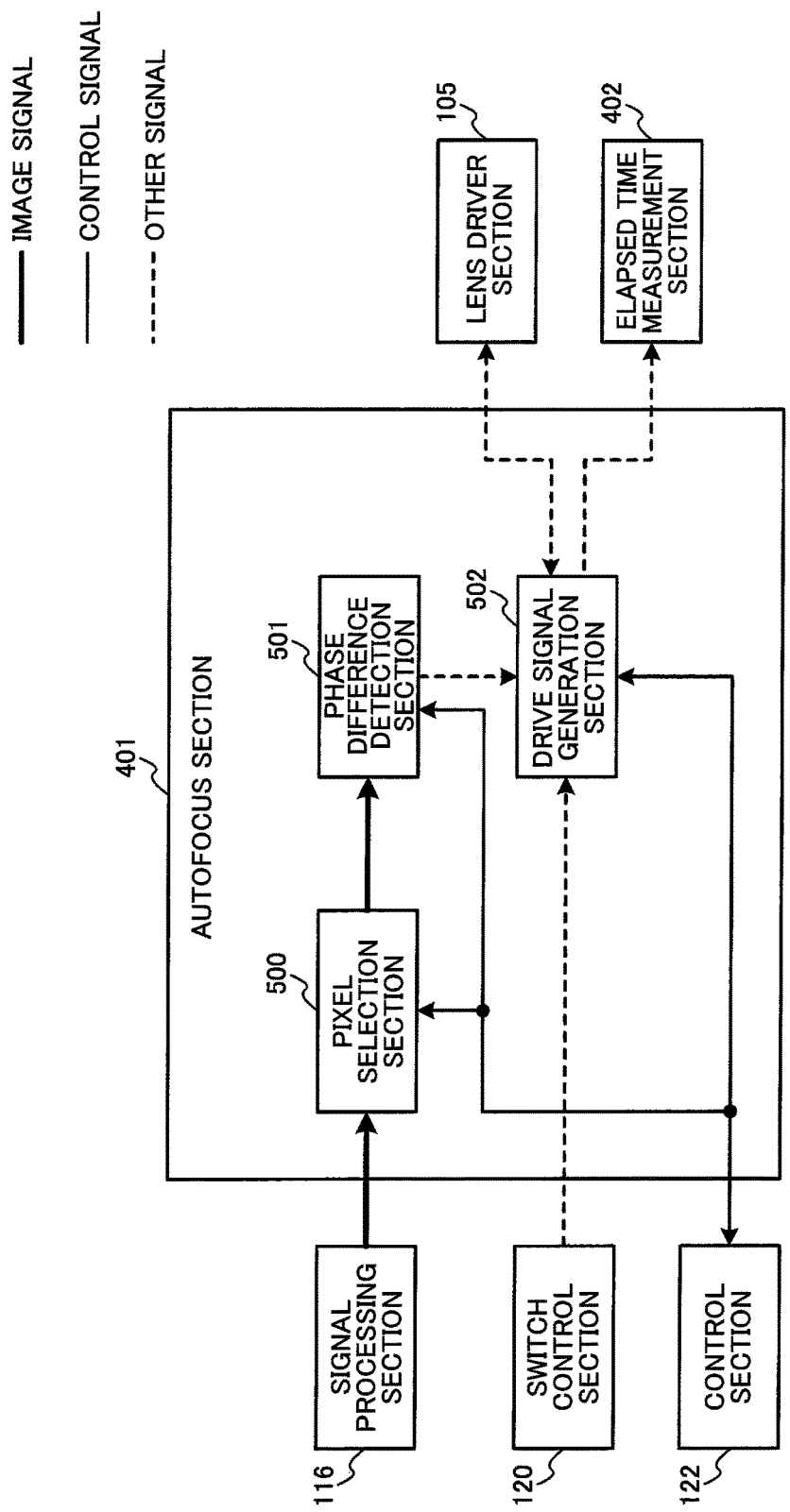
FIG. 10 illustrates another configuration example of an autofocus section.

FIG. 10 illustrates a detailed configuration example of the autofocus section 401. The autofocus section 401 includes a pixel selection section 500, a phase difference detection section 501, and a drive signal generation section 502. The signal processing section 116 is connected to the phase difference detection section 501 through the pixel selection section 500. The phase difference detection section 501 is connected to the drive signal generation section 502. The drive signal generation section 502 is bidirectionally connected to the lens driver section 105. The drive signal generation section 502 is connected to the elapsed time measurement section 402. The switch control section 120 is connected to the drive signal generation section 502. The control section 122 is bidirectionally connected to the pixel selection section 500, the phase difference detection section 501, and the drive signal generation section 502.

The autofocus section 401 according to the second embodiment utilizes the phase detection method disclosed in JP-A-2011-59337 (i.e., the phase difference detection pixels are provided in the image sensor), for example. The image signals output from the signal processing section 116 are transmitted to the pixel selection section 500 under control of the control section 122. The pixel selection section 500 selects the phase difference detection pixel provided in the image sensor, and transmits information about the selected phase difference detection pixel to the phase difference detection section 501 under control of the control section 122. The phase difference detection section 501 detects phase difference information from the phase difference detection pixel, and calculates the moving amount and the moving direction (positive/negative sign) under control of the control section 122. When the moving amount is not 0, the phase difference detection section 501 transmits the moving amount, the moving direction, and a control signal that instructs the drive signal generation section 502 to output a drive signal, to the drive signal generation section 502. The phase difference detection section 501 does not transmit the control signal when the moving amount is 0 (i.e., in-focus state). The drive signal generation section 502 checks the control signals from the switch control section 120 and the phase difference detection section 501 under control of the control section 122. The drive signal generation section 502 transmits the drive signal for moving the in-focus object plane position to the lens driver section 105 when the control signal that causes the autofocus section 401 to start operation has been output from the switch control section 120, and the control signal has been output from the phase difference detection section 501.

The above configuration makes it possible to provide an endoscope apparatus that is configured to normally perform the autofocus control process, and perform the manual focus control process when the user has operated a two-way switch when the desired position cannot be brought into focus by the autofocus control process. The endoscope apparatus according to the second embodiment is configured to perform the autofocus control process without receiving an instruction from the user when a given time has elapsed from the start of the manual focus control process, and a scene change has occurred. Therefore, it is possible to provide an endoscope apparatus with good operability that allows the user to adjust the in-focus object plane position by merely operating a two-way switch without taking account of switching between the autofocus control process and the manual focus control process. It is also possible to provide an endoscope apparatus that implements a stable focus control process by preventing a situation in which the focus control process is switched to the autofocus control process within a short time due to momentary halation or the like.

4. Method According to the Embodiments

According to the above embodiments, the endoscope apparatus includes the focus control section 130 that controls the in-focus object plane position by controlling the optical system (e.g., lens system 103 illustrated in FIG. 2A), the switch control section 120 that switches the focus control process performed by the focus control section 130 between the autofocus control process and the manual focus control process, and the operation section 102 that is operated by the user (i.e., receives an operation performed by the user) (see FIG. 1). When the operation section 102 has been operated by the user during a period in which the focus control section 130 performs the autofocus control process, the switch control section 120 switches the focus control process performed by the focus control section 130 to the manual focus control process, and the focus control section 130 moves the in-focus object plane position to a position that differs from the in-focus object plane position when the operation section 102 has been operated.

The focus control section 130 controls the in-focus object plane position. Since the in-focus object plane position and the state of the optical system (particularly the position of the lens) have a correlation, the focus control section 130 may control the position of the lens. Note that the position of the lens is controlled by outputting the control signal to the lens driver section 105, for example. The focus control section 130 includes the autofocus section 119 and the manual focus section 121 (see FIG. 1). The autofocus section 119 and the manual focus section 121 are controlled to operate exclusively (i.e., only one of the autofocus section 119 and the manual focus section 121 operates). Specifically, the switch control section 120 basically performs a switch control process that causes one of the autofocus section 119 and the manual focus section 121 that currently operates to stop operation, and causes the other of the autofocus section 119 and the manual focus section 121 to start operation.

When the operation section 102 has been operated by the user, the switch control section 120 switches the focus control process performed by the focus control section 130 from the autofocus control process to the manual focus control process, and the focus control section 130 moves the in-focus object plane position. In this case, the user need not separately perform an operation corresponding to the switch control section 120, and an operation corresponding to the focus control section 130. Specifically, the endoscope apparatus according to the above embodiments is not configured so that the switch control section 120 switches the focus control process performed by the focus control section 130 from the autofocus control process to the manual focus control process when the user has performed a first operation, and the focus control section 130 moves the in-focus object plane position when the user has performed a second operation that differs from the first operation, but is configured so that the switch control section 120 switches the focus control process performed by the focus control section 130 from the autofocus control process to the manual focus control process, and the focus control section 130 moves the in-focus object plane position when the user has performed a given operation.

These two processes may be performed in response to a plurality of operations, or may be performed in response to a single operation. The term "single operation" used herein refers to an operation that is considered to be one type of operation for the user. For example, the single operation may be an operation that presses a button once, an operation that presses a lever once, or an operation that turns a dial once in an arbitrary amount. If a single process is performed when an operation that presses something a plurality of times (e.g., double-click operation using a mouse) has been performed, such an operation also falls under the term "single operation". Specifically, an operation that is interpreted by the processing system to be a single operation is considered to fall under the term "single operation". For example, when the user performs a double-click operation by pressing a mouse button twice, the processing system (e.g., PC) interprets the operation as a single double-click operation instead of two single-click operations, and only the process corresponding to the double-click operation is performed. However, since it is undesirable that the single operation be complex from the viewpoint of convenience to the user, the time from the start to the end of the single operation, or the number of operation targets (e.g., buttons) may be limited.

The above configuration makes it possible to effectively control the focus using an operation that is easy for the user to perform. An endoscope apparatus has been designed so that the user determines whether the autofocus control process or the manual focus control process is being performed, and switches the focus control process by issuing an explicit instruction (e.g., by operating the operation section 102). In this case, the user must perform an operation that selects the in-focus object plane position after performing the operation that switches the focus control process to the manual focus control process. However, since it is considered that the user desires to switch the focus control process to the manual focus control process during the autofocus control process when the autofocus control process does not function effectively, it is likely that the in-focus object plane position does not coincide with the position of the object corresponding to the attention area. Therefore, the endoscope apparatus according to the above embodiments is configured so that the user need not separately perform an operation that switches the focus control process from the autofocus control process to the manual focus control process, and an operation that moves the in-focus object plane position. This makes it possible to simplify the configuration of the operation section 102, and simplify the operation performed by the user.

When the operation section 102 has been operated by the user after the switch control section 120 has switched the focus control process performed by the focus control section 130 from the autofocus control process to the manual focus control process, the focus control section 130 may move the in-focus object plane position to a position that differs from the in-focus object plane position when the operation section 102 has been operated by the user.

The operation performed on the operation section 102 may be the same as the above operation that switches the focus control process from the autofocus control process to the manual focus control process, and moves the in-focus object plane position.

The above configuration makes it possible to move the in-focus object plane position to a position that differs from the current position when the operation section 102 has been operated by the user after the focus control process has been switched to the manual focus control process. Therefore, the operation that switches the focus control process to the manual focus control process, and moves the in-focus object plane position, can be the same operation as the operation that moves the in-focus object plane position after the focus control process has been switched to the manual focus control process. This makes it possible to simplify the configuration of the operation section 102, and simplify the operation performed by the user.

The endoscope apparatus may include the scene-change detection section 118 that detects a scene change based on the image signals (captured image) (see FIG. 1). When the scene-change detection section 118 has detected a scene change after the switch control section 120 has switched the focus control process performed by the focus control section 130 from the autofocus control process to the manual focus control process, the switch control section 120 may switch the focus control process performed by the focus control section 130 from the manual focus control process to the autofocus control process.

The term "scene change" used herein includes various types of scene change. For example, the term "scene change" used herein includes a change in the imaging target part of a living body. It may be determined that a scene change has occurred when the imaging target part has changed from the stomach to the small intestine, or changed from the small intestine to the large intestine. Each part may be subdivided into smaller parts (e.g., the large intestine may be subdivided into the transverse colon and the descending colon). In this case, a scene change may be detected based on the color (tone) represented by the image signals.

It may be determined that a scene change has occurred when the object (imaging target) has changed even if the imaging target part has not changed. In this case, a scene change may be detected based on a motion vector, a change in brightness, a change in color (tone), or the like.

It may be determined that a scene change has occurred when the relative positional relationship between the object (imaging target) and the imaging section (end section 101) has changed even if the object has not changed. The relative positional relationship between the object and the imaging section may be the relative distance between the imaging section and the object, or may be the angle formed by the optical axis of the imaging section and the object (i.e., wall surface). Specifically, a scene change may be detected based on whether or not the imaging section is positioned close to the object, or whether or not the imaging section faces directly to the object. In this case, a scene change may be detected based on a change in brightness or the like.

The above configuration makes it possible to switch the focus control process performed by the focus control section 130 to the autofocus control process when a scene change has been detected after the focus control process has been switched to the manual focus control process. It is likely that the user desires to switch the focus control process to the manual focus control process when the autofocus control process does not function effectively. For example, the autofocus control process does not function effectively when a plurality of attention areas are present at a position close to the imaging section and a position away from the imaging section. However, since a scene change is detected when a change in imaging target part, object, relative positional relationship, or the like has occurred, it is considered that the attention area distribution in the depth direction has also changed when a scene change has been detected. Specifically, since the autofocus control process may function effectively due to the scene change, the focus control process is switched to the autofocus control process, and whether or not the autofocus control process functions effectively is determined. In this case, the autofocus control process may also not function effectively after the focus control process has been switched to the autofocus control process. However, since the autofocus control process is convenient to the user as compared with the manual focus control process, there is much point in switching the focus control process to the autofocus control process. Even if the in-focus object plane position after switching the focus control process to the autofocus control process is not satisfactory, it suffices for the user to switch the focus control process to the manual focus control process by performing the above simple operation.

The operation section 102 may include a one-way switch (focus switch 109) (see FIG. 2B). The term "one-way switch" used herein refers to a switch that is turned ON/OFF when operated once by the user.

The above configuration makes it possible to implement the above control operation by operating the one-way switch once. This is particularly effective for the two-step focus switching configuration illustrated in FIG. 3A.

The operation section 102 may include a two-way switch (focus switch 400) (see FIG. 8). The term "two-way switch" used herein refers to a switch that is moved from a standard position to a first position, or moved from a standard position to a second position when operated once by the user. The focus control section 130 may move the in-focus object plane position to a first in-focus object plane position when the two-way switch has been moved to the first position. The focus control section 130 may move the in-focus object plane position to a second in-focus object plane position when the two-way switch has been moved to the second position.

The first position is a position that differs from the standard position, and the second position is a position that differs from the standard position and the first position. The first in-focus object plane position and the second in-focus object plane position are positions that differ from the in-focus object plane position when the operation section 102 has been operated. One of the first in-focus object plane position and the second in-focus object plane position is a far point-side position relative to the in-focus object plane position when the operation section 102 has been operated, and the other of the first in-focus object plane position and the second in-focus object plane position is a near point-side position relative to the in-focus object plane position when the operation section 102 has been operated.

The above configuration makes it possible for the user to designate the moving direction of the in-focus object plane position by performing a single operation. This is particularly effective when the in-focus object plane position can be set to a number of positions (e.g., the four-step focus switching configuration illustrated in FIG. 3B).

According to the above embodiments, the endoscope apparatus includes the focus control section 130, the switch control section 120, the operation section 102, and the scene-change detection section 118 (see FIG. 1). The switch control section 120 switches the focus control process to the manual focus control process when the operation section 102 has been operated when the focus control section 130 performs the autofocus control process. The switch control section 120 switches the focus control process to the autofocus control process when the scene-change detection section 118 has detected a scene change when the focus control section 130 performs the manual focus control process.

The above configuration makes it possible to easily switch the focus control process between the autofocus control process and the manual focus control process. Specifically, the user can switch the focus control process between the autofocus control process and the manual focus control process by merely operating the operation section 102 (i.e., by performing the above simple single operation) when it is considered that the autofocus control process does not function successfully. The autofocus control process that reduces the burden imposed on the user is resumed upon occurrence of a scene change, and the focus control process is switched to the manual focus control process when the operation section 102 has been operated by the user when the autofocus control process does not function effectively.

The endoscope apparatus may include the elapsed time measurement section 402 that measures the elapsed time after the switch control section 120 has switched the focus control process to the manual focus control process (see FIG. 7). When the scene-change detection section 118 has detected a scene change when the focus control section 130 performs the manual focus control process, and the elapsed time is larger than a given threshold value, the switch control section 120 switches the focus control process performed by the focus control section 130 to the autofocus control process.

The above configuration makes it possible to take account of a scene change and the elapsed time as the conditions whereby the focus control process is switched from the manual focus control process to the autofocus control process. When a change in object or a change in relative positional relationship between the object and the imaging section is detected as a scene change, a scene change may be detected even when the user does not intend to change the observation target. For example, a scene change may be detected when the imaging section vibrates due to a shake. In this case, since it is considered that the user continues diagnosis or the like, a situation in which the autofocus control process does not function successfully occurs immediately after the scene change has temporarily occurred.

Specifically, since it is undesirable that the autofocus control process be resumed in such a case, it is desirable to provide a resumption condition in addition to a scene change. The elapsed time can be used as the resumption condition since it is considered that the user does not stop diagnosis or the like (i.e., the user does not intentionally change the scene) immediately after switching the focus control process to the manual focus control process. Specifically, the user switches the focus control process to the manual focus control process when the user feels dissatisfied with the current focus state, and it is considered that the user feels dissatisfied with the current focus state when the attention area (diagnosis/observation target) is present within the captured image.

The switch control section 120 may set the focus control process performed by the focus control section 130 to the autofocus control process when the endoscope apparatus starts operation.

The above configuration makes it possible to give priority to the autofocus control process. Since the autofocus control process can reduce the burden imposed on the user as compared with the manual focus control process, it is advantageous to positively utilize the autofocus control process.

The focus control section 130 may include the contrast calculation section 202 that calculates the contrast value from the captured image, and the drive signal generation section 204 that outputs the drive signal that drives the optical system based on the calculated contrast value. Specifically, the focus control section 130 may include the autofocus section 119 illustrated in FIG. 5, and the autofocus section 119 may include the contrast calculation section 202 and the drive signal generation section 204.

The focus control section 130 may include the phase difference detection section 501 that detects the phase difference information from the captured image, and the drive signal generation section 502 that outputs the drive signal that drives the optical system based on the detected phase difference information. Specifically, the focus control section 130 may include the autofocus section 401 illustrated in FIG. 10, and the autofocus section 401 may include the phase difference detection section 501 and the drive signal generation section 502.

In either case, the focus control section 130 performs the autofocus control process based on the drive signal.

The above configuration makes it possible to utilize a contrast AF method or a phase detection AF method as the autofocus method. Although the first embodiment has been described above taking a combination of the configuration that does not include the elapsed time measurement section 402 and a contrast AF method, and the second embodiment has been described above taking a combination of the configuration that includes the elapsed time measurement section 402 and a phase detection AF method, it is possible to arbitrarily combine the presence or absence of the elapsed time measurement section 402 with the desired AF method. It is also possible to arbitrarily combine the desired discrete N-step focus switching operation (i.e., the desired value N) with the desired AF method.

The focus control section 130 may select one in-focus object plane position among first to Nth (N is an integer equal to or larger than 2) in-focus object plane positions that are set discretely.

The above configuration makes it possible to implement a discrete focus control process. Since the number of selectable in-focus object plane positions is limited, the focus control process can be implemented by a simple operation, and the burden imposed on the user can be reduced.

When the distance from the optical system to an (i+1)-th (1≤i≤N−1) in-focus object plane position is longer than the distance from the optical system to an i-th in-focus object plane position (e.g., when the ID is assigned to each in-focus object plane position (or the lens position corresponding to each in-focus object plane position) in order from the near point at intervals of 1 (see FIGS. 3A and 3B)), the focus control section 130 may include the moving amount setting section 300 that sets the moving amount information that indicates the amount of change in the in-focus object plane position when the operation section 102 has been operated by the user. Specifically, the manual focus section 121 may include the moving amount setting section 300 (see FIG. 6). When information that designates k (k is an integer other than 0) has been set as the moving amount information, the focus control section 130 may change the in-focus object plane position from the i-th in-focus object plane position to the (i+k)-th in-focus object plane position corresponding to the operation performed on the operation section 102.

The above configuration makes it possible to set the moving amount, and implement a discrete focus control process based on the moving amount.

The moving amount setting section 300 may set information that designates −k as the moving amount information when i+k<1 or i+k>N is satisfied. The focus control section 130 may change the in-focus object plane position from the i-th in-focus object plane position to the (i−k)-th in-focus object plane position corresponding to the operation performed on the operation section 102.

The above configuration makes it possible to appropriately move the in-focus object plane position even when the maximum value or the minimum value (farthest point or nearest point) that can be set as the in-focus object plane position is almost reached. When movement beyond the farthest point (nearest point) is instructed, the moving destination can be limited within the allowable range by reversing the value indicated by the moving amount information, and appropriate control can be implemented.

The moving amount setting section 300 may set information that designates 1 or −1 as the moving amount information k.

The above configuration makes it possible to move the in-focus object plane position to the adjacent position, and implement fine control.

The moving amount setting section 300 may set the moving amount information k based on an external input.

The above configuration makes it possible to set the moving amount information k from the user or a system other than the endoscope apparatus, for example.

When the operation section 102 has been operated when the focus control section 130 performs the autofocus control process, and the switch control section 120 has switched the focus control process to the manual focus control process, the focus control section 130 may change the in-focus object plane position from the i-th in-focus object plane position to the (i−k)-th in-focus object plane position.

The above configuration makes it possible for the user to switch the focus control process to the manual focus control process, and move the in-focus object plane position (i.e., move the in-focus object plane position corresponding to the moving amount information k) by operating the operation section 102. The advantages achieved by the above configuration are the same as described above, and further description thereof is omitted.

The operation section 102 included in the endoscope apparatus may include a one-way switch (focus switch 109). Alternatively, the operation section 102 may include a two-way switch (focus switch 400). The details of each switch are the same as described above.

When the operation section 102 includes the two-way switch, the focus control section 130 may change the in-focus object plane position corresponding to the moving amount information k when the two-way switch has been moved to the first position, and may change the in-focus object plane position corresponding to −k obtained by reversing the sign of the moving amount information k when the two-way switch has been moved to the second position. The above configuration illustrates a situation in which the in-focus object plane position is moved toward the far point or the near point corresponding to the operation direction of the switch using the moving amount information. The details thereof are substantially the same as described above, and further description is omitted.

The above embodiments may also be applied to an endoscope apparatus operation device that includes an operation reception section that receives an operation performed by the user on an endoscope apparatus that includes an optical system that is configured so that the in-focus object plane position can be controlled, and an output section that outputs an operation signal that corresponds to the operation performed by the user. The output section outputs the operation signal that instructs to switch the focus control process from the autofocus control process to the manual focus control process, and outputs the operation signal that instructs to move the in-focus object plane position to a position that differs from the in-focus object plane position when the operation reception section has been operated by the user, corresponding to the operation performed by the user. The operation performed by the user may be the above single operation.

The endoscope apparatus operation device corresponds to the operation section 102 illustrated in FIG. 2B, and the operation reception section corresponds to the focus switch 109 (or the focus switch 400 included in the operation section 102 illustrated in FIG. 8), for example. The output section (not illustrated in FIG. 2B and the like) outputs the operation signal to a block that performs the process implemented by the endoscope apparatus. The output section may output the operation signal to the control section 122 illustrated in FIG. 1, for example.

According to the above configuration, the configuration can be simplified since it suffices to provide a single mechanism (e.g., switch) as the operation reception section that allows the user to switch the focus control process from the autofocus control process to the manual focus control process, and move the in-focus object plane position.

The operation reception section may receive a first operation that switches the focus control process from the autofocus control process to the manual focus control process, and moves the in-focus object plane position, and a second operation that moves the in-focus object plane position after the focus control process has been switched to the manual focus control process. The operation reception section may be a one-way switch, and may receive the first operation and the second operation performed using the one-way switch.

According to the above configuration, the first operation and the second operation can be performed using the one-way switch illustrated in FIG. 2B, and an effective focus control process can be implemented by a simple configuration.

The operation reception section may receive a third operation that switches the focus control process from the autofocus control process to the manual focus control process, and increases the distance from the optical system to the in-focus object plane position, and a fourth operation that switches the focus control process from the autofocus control process to the manual focus control process, and decreases the distance from the optical system to the in-focus object plane position.

The operation reception section may receive a fifth operation that increases the distance from the optical system to the in-focus object plane position after the focus control process has been switched to the manual focus control process, and a sixth operation that decreases the distance from the optical system to the in-focus object plane position after the focus control process has been switched to the manual focus control process, in addition to the third operation and the fourth operation.

The operation reception section may be a two-way switch, and may receive the third operation, the fourth operation, the fifth operation, and the sixth operation performed using the two-way switch.

According to the above configuration, the second operation, the third operation, the fourth operation, the fifth operation, and the sixth operation can be performed using the two-way switch illustrated in FIG. 8, and an effective focus control process can be implemented by a simple configuration.

The first embodiment, the second embodiment, and the modifications thereof have been described above. Note that the invention is not limited to the first embodiment, the second embodiment, and the modifications thereof. Various modifications and variations may be made of the first embodiment, the second embodiment, and the modifications thereof without departing from the scope of the invention. A plurality of elements described above in connection with the first embodiment, the second embodiment, and the modifications thereof may be appropriately combined to implement various configurations. For example, an arbitrary element may be omitted from the elements described in connection with the first embodiment, the second embodiment, and the modifications thereof. Arbitrary elements among the elements described in connection with the first embodiment, the second embodiment, and the modifications thereof may be appropriately combined. Any term cited with a different term having a broader meaning or the same meaning at least once in the specification and the drawings can be replaced by the different term in any place in the specification and the drawings. Specifically, various modifications and applications are possible without materially departing from the novel teachings and advantages of the invention.

What is claimed is:

1. An endoscope apparatus comprising:
   an input device that is manually operable by a user;
   an optical system; and
   a computer which controls execution of processes by the endoscope apparatus comprising:
      a focus control process that controls a plurality of in-focus object plane positions by controlling the optical system, the plurality of in-focus object plane positions being set discretely; and
      a switch control process that switches the focus control process between an autofocus control process and a manual focus control process, the in-focus object plane position being automatically controlled when the autofocus control process is performed, and being manually controlled when the manual focus control process is performed;
   wherein the switch control process switches the focus control process from the autofocus control process to the manual focus control process based on a single operation that has been performed by the user on the input device during a period in which the autofocus control process is performed, and
   wherein the focus control process moves the in-focus object plane position based on the single operation to an in-focus object plane position, from among the plurality of in-focus object plane positions, that is adjacent to the in-focus object plane position when the single operation has been performed.

2. The endoscope apparatus as defined in claim 1, wherein when the input device has been operated by the user after the switch control process has switched the focus control process from the autofocus control process to the manual focus control process, the focus control process moves the in-focus object plane position to an in-focus object plane position, from among the plurality of in-focus object plane positions, that differs from the in-focus object plane position when the input device has been operated, and that also differs from the in-focus object plane position that is adjacent to the in-focus object plane position when the input device has been operated.

3. The endoscope apparatus as defined in claim 1, wherein the computer further controls execution of a scene-change detection process that detects a scene change from image signals generated by the endoscope apparatus, and
   wherein when the scene-change detection process has detected a scene change after the switch control process has switched the focus control process from the autofocus control process to the manual focus control process, the switch control process switches the focus control process from the manual focus control process to the autofocus control process.

4. The endoscope apparatus as defined in claim 1, wherein:
   the input device includes a one-way switch, and
   the focus control process moves the in-focus object plane position to an in-focus object plane position, from among the plurality of in-focus object plane positions, that differs from the in-focus object plane position when the one-way switch has been operated once.

5. The endoscope apparatus as defined in claim 1, wherein:
   the input device includes a two-way switch, the two-way switch being a switch that is movable from a standard position to a first position, or movable from the standard position to a second position when operated once by the user, the first position being a position that differs from the standard position, and the second position being a position that differs from the standard position and the first position, and
   the focus control process moves the in-focus object plane position to an in-focus object plane position, from among the plurality of in-focus object plane positions, that differs from the in-focus object plane position when the two-way switch has been operated once.

6. The endoscope apparatus as defined in claim 3, wherein the computer further controls execution of an elapsed time measurement process that measures an elapsed time after the switch control process has switched the focus control process to the manual focus control process, and
   wherein the switch control process switches the focus control process to the autofocus control process when the scene-change detection process has detected a scene change when the manual focus control process is performed and the elapsed time measured in the elapsed time measurement process is larger than a given threshold value.

7. The endoscope apparatus as defined in claim 1, wherein the switch control process sets the focus control process to the autofocus control process when the endoscope apparatus starts operation.

8. The endoscope apparatus as defined in claim 1, wherein:
first to Nth (where N is an integer equal to or larger than 2) in-focus object plane positions are set discretely as the plurality of in-focus object plane positions, and a distance from the optical system to an (i+1)-th (where $1 \leq i \leq N-1$) in-focus object plane position is longer than a distance from the optical system to an i-th in-focus object plane position,
the focus control process includes a moving amount setting process that sets moving amount information that indicates an amount of change in the in-focus object plane position when the input device has been operated by the user, and
the focus control process performs the autofocus control process by changing the in-focus object plane position from the i-th in-focus object plane position to an (i+k)-th (where k is an integer other than 0) in-focus object plane position corresponding to an operation performed on the input device when information that designates k has been set as the moving amount information.

9. The endoscope apparatus as defined in claim 8, wherein:
the moving amount setting process sets information that designates −k as the moving amount information when i+k<1 or i+k>N is satisfied, and
the focus control process performs the autofocus control process by changing the in-focus object plane position from the i-th in-focus object plane position to an (i−k)-th in-focus object plane position corresponding to the operation performed on the input device.

10. The endoscope apparatus as defined in claim 9, wherein the moving amount setting process sets information that designates 1 or −1 as the moving amount information k.

11. The endoscope apparatus as defined in claim 9, wherein the moving amount setting process sets the moving amount information k based on an external input.

12. The endoscope apparatus as defined in claim 9, wherein the focus control process changes the in-focus object plane position from the i-th in-focus object plane position to the (i+k)-th in-focus object plane position when the input device has been operated by the user when the focus control performs process is performing the autofocus control process and the switch control process has switched the focus control process to the manual focus control process.

13. A method for controlling an endoscope apparatus, the endoscope apparatus comprising an input device that is manually operable by a user and an optical system, the method controlling execution of a focus control process that controls a plurality of in-focus object plane positions by controlling the optical system, the plurality of in-focus object plane positions being set discretely, and the method comprising:
receiving an operation performed by the user on the input device; and
switching the focus control process between an autofocus control process and a manual focus control process, and moving the in-focus object plane position based on the operation performed by the user on the input device, the in-focus object plane position being automatically controlled when the autofocus control process is performed, and being manually controlled when the manual focus control process is performed;
wherein the switching switches the focus control process from the autofocus control process to the manual focus control process based on a single operation that has been performed by the user on the input device during a period in which the autofocus control process is performed, and the focus control process moves the in-focus object plane position based on the single operation to an in-focus object plane position, from among the plurality of in-focus object plane positions, that is adjacent to the in-focus object plane position when the single operation has been performed.

* * * * *